US00RE35062E

United States Patent [19]

Brostrom et al.

[11] E Patent Number: Re. 35,062

[45] Reissued Date of Patent: Oct. 17, 1995

[54] FILTER ELEMENT

[75] Inventors: Gerald M. Brostrom; Daniel A. Japuntich; Sabrina M. Yard, all of St. Paul, Minn.

[73] Assignee: Minnesota Mining and Manufacturing Company, St. Paul, Minn.

[21] Appl. No.: 79,234

[22] Filed: Jun. 17, 1993

Related U.S. Patent Documents

Reissue of:

[64] Patent No.: 4,886,058
Issued: Dec. 12, 1989
Appl. No.: 195,029
Filed: May 17, 1988

[51] Int. Cl.[6] ..... A62B 7/00

[52] U.S. Cl. ..... 128/206.12; 128/206.17; 128/206.15; 55/DIG. 35

[58] Field of Search ..... 128/205.27–205.29, 128/206.12, 207.15; 55/DIG. 35

[56] References Cited

U.S. PATENT DOCUMENTS

| | | | |
|---|---|---|---|
| Re. 30,782 | 10/1981 | Van Turnhout | 128/205.27 |
| Re. 321,717 | 6/1986 | Van Turnhout | 128/205.29 |
| 2,206,061 | 7/1940 | Splaine | 128/205.27 |
| 2,220,374 | 11/1940 | Lewis | 128/205.27 |
| 2,227,959 | 1/1941 | Cover | 128/205.29 |
| 2,295,119 | 9/1942 | Malcom et al. | 128/205.27 |
| 2,320,770 | 6/1943 | Cover | 128/146 |
| 3,316,904 | 5/1967 | Wall et al. | 128/206.12 |
| 3,782,083 | 1/1974 | Rosenberg | 128/205.29 |
| 3,803,817 | 4/1974 | Lewis | 128/205.29 |
| 3,971,373 | 7/1976 | Braun | 128/205.27 |
| 4,011,067 | 3/1977 | Carey, Jr. | 128/205.29 |
| 4,133,309 | 1/1979 | Kohler et al. | 128/205.27 |
| 4,133,656 | 1/1979 | Kippel et al. | 128/205.29 |
| 4,141,703 | 2/1979 | Mulchi | 128/206.15 |
| 4,215,682 | 8/1980 | Kubik et al. | 128/205.29 |
| 4,382,440 | 5/1983 | Kapp et al. | 128/205.29 |
| 4,386,948 | 6/1983 | Choksi et al. | 128/205.29 |
| 4,414,973 | 11/1983 | Matheson et al. | 128/206.15 |
| 4,501,272 | 2/1985 | Shigematsu et al. | 128/206.15 |
| 4,543,112 | 9/1985 | Ackley et al. | 128/206.15 |
| 4,572,178 | 2/1986 | Takase et al. | 128/205.27 |
| 4,583,535 | 4/1986 | Saffo | 128/205.29 |
| 4,714,486 | 12/1987 | Silverthorn | 128/205.29 |
| 4,754,751 | 7/1988 | Mausteller et al. | 128/205.28 |
| 4,883,052 | 11/1989 | Weiss et al. | 128/205.29 |

FOREIGN PATENT DOCUMENTS

| | | | |
|---|---|---|---|
| 0197941 | 10/1986 | European Pat. Off. | 128/205.29 |
| 470850 | 9/1937 | United Kingdom | 128/205.29 |
| 573951 | 12/1945 | United Kingdom | 128/205.29 |
| 1041394 | 9/1966 | United Kingdom | 128/205.29 |

OTHER PUBLICATIONS

DIN 3181 Part 2, "Atemfilter fur Atemschultzgerate", (Mar. 1980).
BS 2090 "Respirators for Protection Against Harmful Dusts and Gases", (1969).
BS 4555 "High Efficiency Dust Respirators", (1970).
20 CFR 11 Subpart K, Sect. 11.130–11.140–12, (1987).
30 CFR 11 Subpart K, sect. 11.140–4, (1987).
30 CRF 11 Subpart K, 11.140–9, (1987).
30 CFR 11 Subpart K, 11.140–11, (1987).
30 CFR 11 Subpart K, 11.140–6, (1987).
Military Specification, "Filter Element Set, Chemical–Biological Mask, M13A2", MIL–F–51425A(EA), 10 Sep. 1986.

*Primary Examiner*—Kimberly L. Asher
*Attorney, Agent, or Firm*—Gary L. Griswold; Walter N. Kirn; Carole Truesdale

[57] ABSTRACT

A filter element adapted for attachment to a respirator face piece which includes front and rear walls of filter material, a breather tube, and a porous inner layer which maintains the front and rear walls in a spaced-apart relationship over substantially their entire area and which functions to evenly distribute air flow across the available filter element surface area.

39 Claims, 2 Drawing Sheets

FILTER ELEMENT

Matter enclosed in heavy brackets [ ] appears in the original patent but forms no part of this reissue specification; matter printed in italics indicates the additions made by reissue.

TECHNICAL FIELD

The present invention relates to filtration elements used in respirators or face masks. In another aspect, the present invention relates to filtration face masks or respirators with detachable filtration elements.

BACKGROUND

Filtration face masks or respirators are used in a wide variety of applications when it is desired to protect a human's respiratory system from particles suspended in the air or from unpleasant or noxious gases.

Filter elements of respirators my be integral to the body of the respirator or they may be replaceable, but in either case, the filter element must provide the wearer with protection from airborne particles or unpleasant or noxious gases over the service life of the respirator or filter element. The respirator must provide a proper fit to the human face without obscuring the wearer's vision and it is desirable that a respirator require a minimum of effort to draw air in through the filter media. This is referred to as the pressure drop across a mask, or breathing resistance.

To achieve the levels of filter performance such as those defined in 30 C.F.R 11 subpart K §§11.130–11.140–12 (1987), DIN 3181 Part 2, "Atemfilter für Atemschultzgeräte" (March, 1980), BS 2091, "Respirators for Protection Against Harmful Dusts and Gases" (1969), and BS 4555, "High Efficiency Dust Respirators" (1969) the number of layers of filter material, filter material type, and available filtration area are important factors in filter element design. The present invention provides a means of more fully utilizing a filter element's available filtration area by properly managing air flow through the filter material of the filter element. Proper management of air flow can also prevent premature loading of the filter material immediately opposite the breather or inhalation tube, which can cause the filter element to collapse over the breather tube, thereby restricting inhalation and shortening the service life of the fiber element.

Various filter element designs have been proposed to provide as much filter surface area as possible while minimizing the obstruction to the wearer's vision, and/or the pressure drop across the mask. U.S. Pat. No. 2,320,770 (Cove) discloses a respirator with detachable filter elements. The filter elements are preferably rectangular and are made from a sheet of filter material with all open sides sewn closed. The filter element has a hole adapted to be attached to the body of the mask. Cover asserts that after being sewn, the filter element can be turned inside out so the seams and folds cause the bag to assume a shape and curvature which tends to keep the sides of the bags apart without the aid of an additional spacing element. Incoming air is apparently intended to travel through either the front or back sides of the bag into the space between these sides and then through the hole inside the mask. U.S. Pat. No. 2,220,374 (Lewis) discloses a respirator which includes a rigid mask and a face mold attached to the mask. The rigid mask includes an air inlet opening and filtering means covering the opening. The filtering means comprises a shell having perforations on at least three sides, filtering material located inside the shell and a filter spreading member adapted to hold the filtering material in a position exposing the filtering material to direct contact with the air entering the perforations. U.S. Pat. No. 2,295,119 (Malcom et al.) discloses a respirator comprising a face piece adapted for the wearer's nose and mouth attached to two removable, egg-shaped filter boxes. The filter boxes have inner and outer, perforated members or covers which form a filter chamber, and two filter elements positioned between the inner and outer members of the filter box whose peripheral portions are compressed and sealed between the outer and inner members of the filter box. One of the filter elements is at attached to the filter box and face piece by a locking member which secures the filter element around the air entrance opening of the face piece. Preferably, the filter box also includes a means to engage the outer filter element and space it from the inner filter element inside the filter box such as a member in the shape of a reverse curve which is pan of the locking member which clamps the filter material around the air entrance opening of the face piece. U.S. Pat. No. 2,206,061 (Splaine) discloses a respirator comprising a face piece adapted to fit over the nose and mouth of the wearer which is adapted to fit into the open ends of two filters. The filters extend laterally in opposite directions from the face piece. The filters are relatively narrow, tapering from a rounded end at the bottom towards the top so that the side walls substantially meet at the top edge and contain light coil spring extending along the bottom portion of each filter to help keep the filters in an expanded condition. U.S. Pat. No. 4,501,272 (Shigematsu et al.) discloses an embodiment of a dust-proof respirator with an intake chamber assembly comprising an intake cylinder fitted airtight into a mounting mouth of a mask body with a front wall positioned opposedly to the intake cylinder and a rear wall composed of a filtration medium fastened to the intake cylinder and along the peripheral edge of the front wall. Filtration medium is also fastened to the front of the intake chamber, resulting in increased filtration area.

The present invention provides, in an easily manufactured form, a filter element of compact size and a nature capable of low air flow resistance and high filtration efficiency which satisfies various performance specifications of U.S. and foreign countries some of which have been set forth above. None of the prior art teaches a combination of features like those of the present invention having the advantages of the present invention.

SUMMARY OF THE INVENTION

The present invention provides a filtration element comprising (A) substantially coextensive front and rear walls joined to each other along their peripheral edges, and each comprising at least one layer of filter material, (B) a porous layer, hereinafter occasionally referred to as a baffle component, contained between the front and rear walls which is substantially coextensive with the walls, which maintains the walls in a spaced-apart relationship to one another substantially over their entire area, and which contributes no more than 50% of the total pressure drop across the filter element, and (C) a breather tube bonded to the rear wall of the filter element and having a means of attachment for securing the filter element to a respirator face piece.

An advantage of the filter elements as described is that they be adapted to perform at high efficiency levels with respect to the filtration of dusts, mists, or fumes without producing large pressure drops.

One embodiment of the filter element of this invention will permit no more than 1.5 mg penetration of silica dust with a geometric mean particle diameter of 0.4–0.6 micrometer, over a 90 minute period, at a flow rate of 16 liters/min., measured in accordance with procedures set out 30 C.F.R. 11 subpart K §11.140–4 (1987) and will have a pressure drop across said filter element before the 90 minute period of no more than 30 mm $H_2O$ and after the 90 minute period of no more than 50 mm $H_2O$ where said pressure drops are measured in accordance with the procedures set forth in 30 C.F.R. 11 subpart K §11.140–9 (1987). A second embodiment of the filter element of this invention will permit no more than about 3.0 percent penetration of 0.3 micrometer diameter particles of dioctyl phthalate (DOP), and preferably no more than about 0.03 percent, contained in a stream at a concentration of 100 microgram/l, at a flow rate of 42.5 liters/min. measured in accordance with the procedures set forth in 30 C.F.R. 11 subpart K §11.140–11 (1987) and permit no more silica dust penetration and no greater pressure drops before or after the 90 minute period than those levels set out above measured in accordance with the procedures specified above. A third embodiment of the filter elements of this invention will permit no more than 1.5 mg of lead fume penetration, measured as the weight of lead, through a filter element over a 312 minute period at an air flow rate of 16 liters/min and will have a pressure drop before the 312 minute period of no more than 30 mm $H_2O$ and after the 312 minute period of no more than 50 mm $H_2O$ measured in accordance with the procedures set forth in 30 C.F.R. 11 subpart K §§11.140–6 and 11.140–9 (1987).

DETAILED DESCRIPTION OF THE INVENTION

Figure 1:
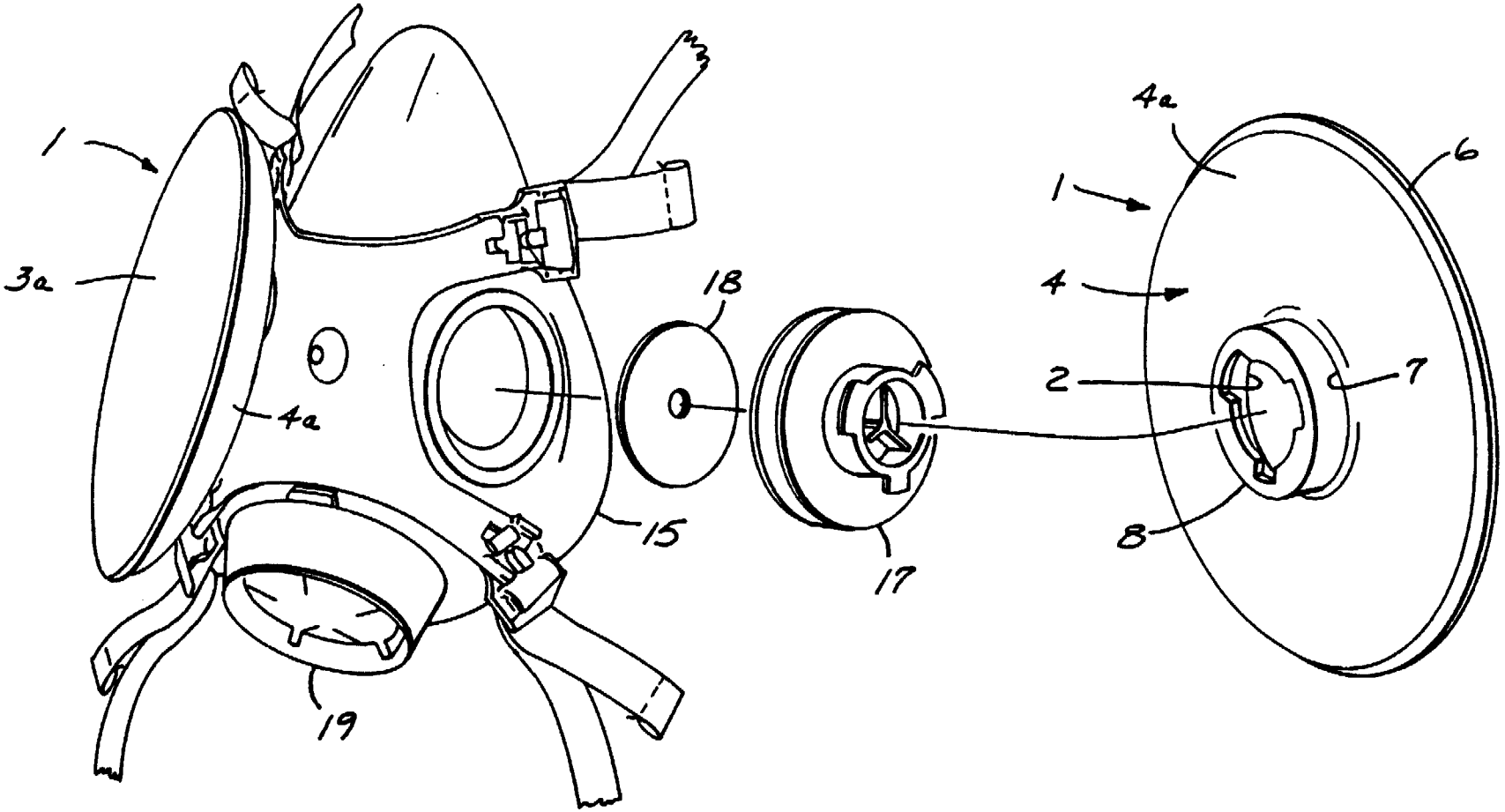
FIG. 1 is a half-mask respirator fitted with filter elements of the present invention, one of which is shown in an exploded manner to illustrate a means by which the filter elements can be joined to the respirator face piece.
Figure 2:
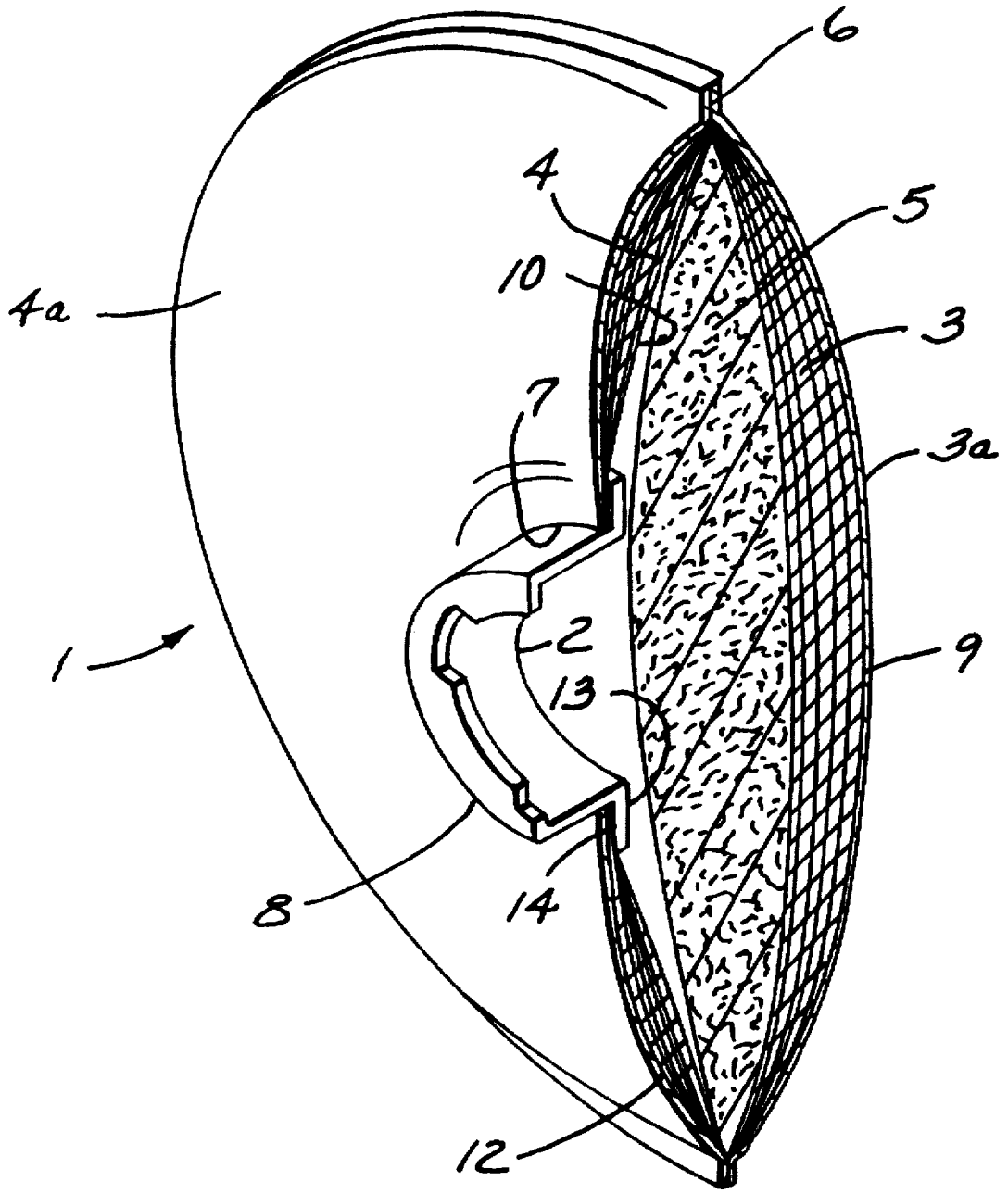
FIG. 2 is a cross-section of a representative filter element of the invention.

The filter element 1 of this invention comprises front wall 3, a rear wall 4, and layer of porous material 5 serving to spsce the front and rear walls and functioning as a baffle component to more evenly distribute air flow through the filter element, and a breather tube 8. The front wal1 3, rear wall 4, and baffle component 5 are substantially coextensive with each other and said baffle component 5 is contained between the front and walls 3,4. The filter element 1 can have various shapes such as round, rectangular, or oval, but preferably, the filter element is round as depicted in FIGS. 1 and 2. Filter element size can vary depending upon the materials of construction selected for the filter element 1 and upon various design and performance criteria known to those skilled in the art, e.g., the desired pressure drop across the filter, and the type and amount of dust, mist, or fumes to be removed from the wearer's inhaled air. However, the shape and size of a filter element should not obstruct the wearer's eyesight when mounted on the respirator face piece 15. The front and rear walls 3,4 are joined along their peripheral edges by a number of bonding methods such as thermomechanical methods (e.g., ultrasonic welding), sewing, and adhesive such that a bond 6 is formed that prevents the leakage of air into or out of the filter element 1. Preferably, the baffle component 5 is also joined to the front and rear wall 3,4 through the bond 6.

The filter element 1 has a breather tube 8 which can have various shapes and can be formed from various materials such as synthetic resin or rubber. Preferably the breather tube is made of a synthetic resin which is heat sealable, e.g., polypropylene and is cylindrical in shape. The breather tube 8 can be mounted anywhere along the interior 10 or exterior 12 surface of the rear wall 4 but preferably the breather tube 8 is mounted centrally to the interior surface 10 of the rear wall 4. The breather tube 8 may be mounted to the chosen wall surface 10 or 12 using any suitable means, e.g., adhesive or ultrasonic welding. The rear wall 4 has an opening 7 adapted to fit the breather tube 8. The breather tube 8 is bonded to the rear wall 4 to prevent air leakage into or out of the filter element 1. Preferably, the breather tube 8 has a flange 13 on the end of the breather tube 8 articulating with the interior surface 10 of the rear wall 4. This flange 13 provides a convenient surface 14 for bonding to the interior surface of the rear wall 10. The other end of the breather tube 8 can be adapted to either join directly with the respirator face piece 15, or as illustrated m FIG. 1, to join to an adapter 17 which is joined to the respirator face piece 15. One advantage of this invention is that the wearer can conveniently test the fit or airtightness of the seal between the wearer's face and the face piece 15 by pressing against the exterior surface 9 of the front wall 3 opposite the breather tube 8 to cause the front wall 3 and baffle component 5 to collapse against the breather tube opening 2 thereby blocking off air flow through the filter element 1. The wearer then inhales while the face piece 15 is held against his face thereby creating a negative pressure differential in the face piece. The wearer can then determine whether there are leaks between the face piece 15 and his face because these areas will fail to seal. Since it is most convenient for the wearer to press against the front wall with his hand, and more preferably with one or more of his fingers, the inner diameter CID) of the breather tube is preferably 1.0 to 4.0 cm, and more preferably 1.5 to 3.5 cm. However, for any particular filter element construction, e.g., filter element diameter, materials of construction, filter element thickness, and breather tube outer diameter (OD) the smaller the breather tube (ID), the larger the pressure drop across the filter element.

Optionally, the breather tube 8 may include a valve, typically a diaphragm valve 18 as depicted in FIG. 1. The valve allows the wearer to draw filtered air out of the filter element 1 into the respirator face piece 15 but prevents the wearers exhaled air from entering the filter element 1, thereby directing exhaled air out of the face piece 15 through an exhalation point such as an exhalation valve 19. Preferably, the optional valve is part of the respirator face piece 15 or the adapter 17.

The front and rear walls 2,4 are comprised of material which can function as filter material, with or without an outer cover or scrim. The selection of the materials of construction for the front and rear walls 3,4 will depend upon design factors well known to those skilled in the art, such as the type of environment in which a respirator equipped with the filter elements is to be used, and performance requirements such as the pressure drop across the respirator, the type and mount of dust, mist, or fume to be removed from the wearer's inhaled air, and design requirements set out in 30 C.F.R. 11, subpart K §§11.130–11.140–42 (1987), herein incorporated by reference. While the front and rear walls 3,4 of the filter element 1 can each be comprised of only a single layer of filter material, a plurality of layers is preferred for high performance filter elements. By using a plurality of layers of filter material, web irregularities which could lead to premature penetration of particles though a single layer of filter material can be minimized. However, very thick walls should be avoided because they create problems in assembling the filter element 1 and could cause the filter element 1 to become so thick that it could obstruct the wearer's vision when in use. Examples of suitable filter material include nonwoven web, fibrillated film web, air-laid web, sorbent-particle-loaded fibrous web such as those described in U.S. Pat. No. 3,971,373 (Braun), glass filter paper, or combinations thereof. The filter material my comprise, for example, polyolefins, polycarbonate, polyesters, polyurethanes, glass, cellulose, carbon, alumina or combinations thereof. Electrically charged nonwoven microfiber webs (See U.S. Pat. No. 4,215,682 (Kubik et al.) or U.S. Pat. No. Re. 30,782 (Van Turnhout)) are especially preferred. A filter material comprising a plurality of layers of charged, blown polyolefin microfiber (BMF) web is preferred, with an electrically charged polypropylene web being more preferred. Carbon-particle- or alumina-particle-loaded fibrous webs, are also preferred filter media for this invention when protection from gaseous materials is desired.

The front and rear walls 3, 4 preferably include outer cover layers 3a, 4a respectively which my be made from any woven or nonwoven material such as spunbonded web, thermally bonded webs (e.g., air-laid or carded), or resin-bonded webs. Preferably, the cover layers are made of spun-bonded or carded, thermally bonded webs with high hydrophobicity such as those made of polyolefins, e.g., polypropylene. The cover layers protect and contain the filter material, and may serve as an upstream prefilter layer.

The baffle component 5 maintains the front and rear walls 3,4 in a substantially spaced-apart relationship and also causes inhaled air to be drawn more evenly across the filter element 1. This results in more even loading of dust, mist, or fumes contained in inhaled air across the entire area of the filter element 1, in longer filter element service life, and for a given filter element construction, lower pressure drops across the filter element 1. The baffle component 5 can be made of woven or nonwoven webs, loose fibers, fiber batts, loose particulate material, e.g., carbon particles, particulate material bonded, e.g., with polyurethane together in a porous matrix, or combinations thereof. The baffle component material contained between the front and rear walls forms a porous layer that contributes no more than 50%, and preferably no more than 30%, of the pressure drop across the filter element. Examples of suitable baffle component materials are glass filter paper, air-laid webs, carded webs, fibrillated film webs, sorbent-particle-loaded fibrous webs, bonded sorbent particle matrices, or combinations thereof. Preferably, the baffle component 5 comprises compressable, resilient, nonwoven web such as those formed by performing carding or air laying operations, (e.-g., Rando Webbers) on blends of staple and binder fibers such that the fibers are bonded together at points of fiber intersection after the operation. The baffle component 5 can be made from natural materials such as glass, cellulose, carbon, and alumina, synthetic materials such as polyester, polyamide, and polyolefin, polycarbonate, polyurethane, or combinations thereof. Preferably, the baffle component 5 comprises polyester or polyolefin. Also preferred when protection from hazardous gases or vapors is desired are sorbent-particle-loaded fibrous webs, and particularly carbon- or alumina-particle loaded webs, or sorbent-particles, e.g., carbon or alumina which may or may not be bonded together.

The baffle component 5 should have sufficient void volume or porosity, and be thin enough to prevent the pressure drop across the filter element from becoming unacceptably high. It should also be thin enough to make assembly of the filter element 1 easy and to prevent the filter element 1 from becoming so thick that it obstructs the wearer's vision when the filter element 1 is mounted on a respirator face piece. One skilled in the art will understand that the maximum acceptable pressure drop across the filter element 1 is determined by the comfort requirements of the wearer, and that as a practical matter, sometimes these pressure drops are determined by the standards, and measured according to the procedures set out in 30 C.F.R. 11, subpart K §§11.130–11.140–12 (1987). The proper selection of baffle component thickness and baffle component structural features (i.e., percent solidity defined by the equation, % solidity= 100×[density of the porous layer/density of the material used to make the porous layer], fiber diameter or particle size, and material of construction) can provide a thin baffle component 5, which if compressible is resilient, and is rigid enough to support the front and rear wails 3,4 in a spaced-apart relationship while maintaining an acceptable pressure drop across the filter element 1 and while functioning to evenly distribute dust, mist, or fume loading across the filter element 1 surface. A thin baffle component also permits a thinner filter element which will be less obstructive to the wearer's vision. Generally, the baffle component 5 should be 0.2 cm to about 4.0 can thick, and preferably 0.3 cm to 1.3 cm thick. Preferably, a baffle component 5 comprising a nonwoven material should have at least a 10 micrometer average fiber diameter and a solidity of 11 percent or less.

Filter elements of the present invention are further described by way of the non-limiting examples below.

EXAMPLES

The silica dust loading test was performed in accordance with 30 C.F.R. 11subpart K §11.14–4.

The lead fume test was performed in accordance with 30 C.F.R. 11 subpart K §11.140–6.

The DOP filter test was performed in accordance with 30 C .F.R. subpart K §11.140–11.

Pressure drops across the filter elements were determined in accordance with procedures described in 30 C.F.R. 11 subpart K §11.140–9.

Filter elements were assembled by cutting the appropriate diameter circular front and rear walls, baffle component, and any cover layers from various materials which are specified below. A hole approximately 3.27 cm in diameter was cut through the rear wall of each filter element and the cover layer, if any, covering the rear wall. Each filter element had a cylindrical, 3.27 cm OD, 3.14 cm ID, 0.572 cm cut long, polypropylene breather tube with a 0.526 cm wide flange around the outer diameter of one end. The unflanged end of the breather tube was inserted through the hole in the rear wall and any cover layer and pulled through the hole until one surface of the flange contacted the interior surface of the rear wall. This flange surface was then bonded to the rear wall surface. Where the rear wall material was a polypropylene blown microfiber (BMF) web, the flange was ultrasonically welded using a Branon ultrasonic welder to the interior surfare of the rear wall. Where the rear wall was made of a fiberglass material, the flange was bonded to the interior surface of the rear wall using a layer of 3M Jetmelt® adhesive 3764. The various layers were assembled in a sandwich like structure where the baffle component was the innermost layer surrounded by the front and rear walls, and any cover layers fomed the outermost layers of the sandwich. The peripheral edges of the polypropylene BMF, front and rear walls and baffle component were then ultrasonically welded together. The peripheral edges of the front and rear walls and baffle component of the filter element made with fiberglass paper were sealed using the hot melt adhesive described above.

EXAMPLES 1–12

The effect of fiber diameter and percent solidity of a nonwoven baffle component on pressure drop across the filter element is illustrated by the following examples. Circular filter elements 10.16 cm in diameter with front and rear walls made of six layers of electrically charged polypropylene BMF web similar to that described in U.S. Pat. No. 4,215,682 (Kubik et al.), basis weight of approximately 55 g/m$^2$ were constructed. The baffle components were 0.51 cm thick and were made of web which was prepared by carding blends of polyester (PET) staple fiber of the specified diameter, and binder fibers (i.e. a sheath/core fiber comprising a polyester terephalate core having a melting temperature of approximately 245° C. and a sheath comprising a copolymer of ethylene terephthalate and ethylene isophthalate, available as Melty Fiber Type 4080 from Unitika Ltd, Osaka Japan) of various diameters, in a 65:35 PET/binder fiber weight ratio and subsequently placing the carded web in a circulating air oven at 143° C. for about 1 minute to activate the binder fibers and consolidate the web. The various solidities, of the baffle component, fiber diameters of the PET and binder fibers, and average fiber diameters of the fiber blends used in the baffle component web are summarized in Table 1. The filter elements were assembled according to the procedure described above. Pressure drops were measured for each filter element using the procedure referenced above. The pressure drops are summarized in Table 1.

TABLE 1

| Example | Nominal staple fiber diameter (micrometers) | Nominal binder fiber diameter (micrometers) | Ave. fiber diameter micrometers) | Web solidity (%) | Pressure drop mm $H_2O$) |
|---|---|---|---|---|---|
| 1 | 39.3 | 39.3 | 39.3 | 0.84 | 21.1 |
| 2 | 39.3 | 39.3 | 39.3 | 1.38 | 23.4 |
| 3 | 39.3 | 39.3 | 39.3 | 1.60 | 19.5 |
| 4 | 23.8 | 24.9 | 24.2 | 0.84 | 25.5 |
| 5 | 23.8 | 24.9 | 24.2 | 1.44 | 29.0 |
| 6 | 23.8 | 24.9 | 24.2 | 1.89 | 28.6 |
| 7 | 17.6 | 20.3 | 18.6 | 1.06 | 23.9 |
| 8 | 17.6 | 20.3 | 18.6 | 1.63 | 31.6 |
| 9 | 17.6 | 20.3 | 18.6 | 2.13 | 36.5 |
| 10 | 13.4 | 14.3 | 13.8 | 0.83 | 40.8 |
| 11 | 13.4 | 14.3 | 13.8 | 1.25 | 33.3 |
| 12 | 13.4 | 14.3 | 13.8 | 1.79 | 43.5 |

The data shows that both the average fiber diameter and solidity of the nonwoven material comprising the baffle component affects the pressure drop across the filter element and that fiber diameters as low as 13.8 micrometers produced acceptably low filter element pressure drops.

EXAMPLES 13–16

Circular filter elements similar to those described in Examples 1–12 were assembled except that these filter elements had baffle components made of woven (scrim) and nonwoven materials of various thicknesses. The woven web used to made the baffle components was a polypropylene rectangular mesh scrim 0.05 cm thick commercially available from Conwed as ON 6200. The nonwoven web used for the baffle component was made according to a similar procedure used to made the nonwoven baffle web used in Examples 1–12 except that a 50:50 blend of a 51 micrometer diameter polyester staple fiber and 20.3 micrometer diameter, Eastman T-438, polyester binder fiber was used, and the web was calendered to a thickness of 0.07 cm after it came out of the oven. The pressure drops across the filter elements were measured according to the procedure referenced above. The baffle component materials and pressure drops are reported in Table 2.

TABLE 2

| Example | Baffle type | Solidity (%) | Thickness (cm) | Pressure drop (mm $H_2O$) |
|---|---|---|---|---|
| 13 | Scrim[a] (1 layer) | 8.1 | 0.05 | >100 |
| 14 | Scrim[a] (4 layers) | 8.1 | 0.20 | 29 |
| 15 | Nonwoven[b] (3 layers) | 10.7 | 0.20 | 55 |
| 16 | Nonwoven[b] (6 layers) | 10.7 | 0.41 | 29 |

[a]woven scrim
[b]polyester nonwoven web

The data shows that woven and nonwoven baffle components with solidifies as high as 8–10.7 % and thickness as low as 0.2 cm produced filter elements having acceptable pressure drops. The data also shows that baffle component solidity and thickness affect the pressure drop across the filter, so both should be considered when selecting baffle component material.

EXAMPLES 17–22

7.6, 10.2 and 12.7 cm diameter filter elements were prepared in the manner described above except that one set of filter elements with these diameters had front and rear walls made of two single layers of fiber glass paper (available from Hollingsworth & Vose, #HE 1021 Fiberglass Paper) and another set of filter elements with the same diameters had walls made of a single layer of the same electrically charged polypropylene BMF web used in Examples 1–12. The nonwoven web used for the 0.64 cm thick baffle components used in each filter element was made according to a similar procedure used to make the nonwoven baffle web used in Examples 1–12 except that a 20.3 micrometer diameter, Melty Fiber binder fiber was used. The filter elements were subjected to the silica dust loading test referenced above. Dust penetration and initial and final pressure drops were measured and are reported in Table 3. After testing, the filters were inspected to determine the evenness of particulate loading across the surface of the filter element. The inspected filters were evenly loaded with particulate material over both the surfaces of the front and rear walls.

TABLE 3

| Example | Filter media | Filter dia. (cm) | Pen. (mg) | Initial pressure drop (mm $H_2O$) | Final pressure drop (mm $H_2O$) |
|---|---|---|---|---|---|
| 17 | Fiberglass | 7.6 | 1.45 | 10.1 | 33.4 |

TABLE 3-continued

| Example | Filter media | Filter dia. (cm) | Pen. (mg) | Initial pressure drop (mm $H_2O$) | Final pressure drop (mm $H_2O$) |
|---|---|---|---|---|---|
| 18 | Fiberglass | 10.2 | 1.49 | 6.3 | * |
| 19 | Fiberglass | 12.7 | 2.94 | 4.6 | 6.7 |
| 20 | BMF | 7.6 | 0.22 | 5.8 | 15.8 |
| 21 | BMF | 10.2 | 0.15 | 3.7 | 4.8 |
| 22 | BMF | 12.7 | 0.18 | 2.8 | 3.1 |

*Filter broke

The data demonstrates that charged polypropylene BMF filter media permits less penetration of silica dust during the test period and produces lower pressure drops across the filter element over the test period than fiberglass paper. Therefore, filter elements utilizing the BMF media can be made in smaller sizes and still offer comparable performance levels to larger filter elements using the fiberglass media.

EXAMPLES 23–26

Three circular filter elements having diameters of 7.6, 10.2 and 12.7 cm were constructed according to the procedure described above, using front and rear walls made of two single layers of fiberglass paper (available from Hollingsworth & Vose, #HE 1021 Fiberglass Paper), and baffle components 0.64 cm thick, made of nonwoven baffle component web identical to that used in Examples 17–22. Additionally, three circular, 10.2 cm diameter filter elements were constructed using front and rear walls made of a single layer of the same electrically charged polypropylene BMF web used in Examples 1–12 and 0.64 cm thick baffle components made of the same nonwoven baffle component web used in Examples 17–22. The filter elements used in Example 26 also incorporated a cover layer over the front and rear walls made of material similar to the baffle component web used in Examples 17–22, except that the web was calendered to a thickness of 0.033 cm after it came out of the oven. The filters were assembled and subjected to the lead fume loading test referenced above. Initial and final pressure drops across the filter elements and the level of lead fume penetration through the filters were measured. After testing, the filter elements were visually inspected to determine if there had been even loading of the lead fume across the surface of loaded across both the front and rear wall surfaces.

Filter construction diameter and lead fume penetration test data are reported in Table 4.

TABLE 4

| Example | Filter media | Filter dia. (cm) | Pen. (mg) | Initial Pressure drop (mm $H_2O$) | Final pressure drop (mm $H_2O$) |
|---|---|---|---|---|---|
| 23 | Fiberglass | 7.6 | 0.30 | 10.8 | >115 |
| 24 | Fiberglass | 10.2 | 0.30 | 6.2 | >115 |
| 25 | Fiberglass | 12.7 | 0.22 | 4.9 | >115 |
| 26* | BMF | 10.2 | 0.28 | 3.2 | 41.5 |

*average of three samples

The data shows that the polypropylene, BMF filter media provides the wearer with protection against lead fumes with significantly lower pressure drops than filter elements made with fiberglass media.

EXAMPLES 27–35

Circular filter elements ranging in diameter from 7.6 to 10.2 cm were constructed using a single layer of fiberglass paper (available from Hollingsworth & Vose, Hovoglas® #HB-5331 Fiberglass Paper) for front and rear walls and a 0.64 cm thick baffle component made of the same web as the baffle components used in Examples 23–26. Additionally, a set of circular filter elements ranging in size from 7.6 to 10.2 cm diameter with front and rear walls made of a plurality of layers of the same electrically charged polypropylene BMF used in Examples 1–12 and a 0.64 cm thick baffle component made of the same web as the baffle components used in Examples 23–26 were constructed in accordance with the procedure described above. All of the filter elements were subjected to the DOP penetration test referenced above. The filter wall material, number of layers of filter material, filter diameter, DOP penetration, and pressure drops across the filter measured after the DOP penetration test are summarized in Table 5.

TABLE 5

| Example | Filter Media | Layers of filter media | Filter Dia. (cm) | Pen. (%) | Final pressure drop (mm $H_2O$) |
|---|---|---|---|---|---|
| 27 | Fiberglass | 1 | 11.4 | 0.015 | 27.5 |
| 28 | BMF | 5 | 7.6 | 0.013 | 29.5 |
| 29 | BMF | 5 | 8.3 | 0.006 | 25 |
| 30 | BMF | 6 | 10.2 | 0.001 | 20.5 |
| 31 | BMF | 5 | 10.2 | 0.004 | 16.5 |
| 32 | BMF | 4 | 10.2 | 0.011 | 13.0 |
| 33 | BMF | 4 | 7.30 | 0.10 | 25.0 |
| 34 | BMF | 2 | 7.6 | 2.5 | 12 |
| 35 | BMF | 1 | 7.6 | 30.0 | 5 |

EXAMPLE 36

Five, 10.2 cm diameters circular filter elements were made which were identical to those used in Example 30. The filters were subjected to the silica dust test referenced above. The average silica dust penetration through the filter elements was 0.05 mg, the average pressure drop across the filter element before the test was 20.5 mm $H_2O$, and the average pressure drop across the filter element area the test was 22.4 mm $H_2O$. After the test the filter elements were visually inspected to determine the evenness of particle loading on filter evenly loaded with silica dust over both the front and rear walls of the filter element.

EXAMPLES 37–41

Circular filters elements similar to those described in Examples 1–12 were assembled except that these filter elements had baffle components made of particles of various diameters and materials. The particulate material when held between the front and rear walls formed a porous layer. Several of the examples were carbon particles classified by sieving. One of the examples was polybutylene resin pellets of uniform size. The pressure drop across the filter elements were measured according to the procedure referenced above, The baffle component materials and pressure drops are reported in Table 6.

TABLE 6

| Example | Baffle material | Average particle diameter (mm) | Thickness (cm) | Pressure drop (mm $H_2O$) |
|---|---|---|---|---|
| 37 | carbon | .93 | .99 | 47.0 |
| 38 | carbon | 1.09 | .86 | 40.1 |
| 39 | carbon | 1.29 | .89 | 33.9 |
| 40 | carbon | 1.7 | .91 | 32.6 |
| 41 | polybutylene | 3.0 | 1.02 | 24.7 |

The data shows that there is a definite relationship between diameter and pressure drop. Particle sizes above 1.5 mm will give acceptable pressure drops.

EXAMPLES 42

Filter elements 10.2 cm in diameter were constructed using front and rear walls of a single layer of the polypropylene BMF web used in Examples 1–12 and 0.64 cm thick baffle components made of the same nonwoven baffle component web used in Examples 17–22. Each filter element had a cylindrical, polypropylene breather tube. The breather tubes had various inner diameter but their outer diameter was 3.27 cm. The filter elements were assembled according to the procedure described above and the pressure drop across each filter element was measured according to the procedure referenced above. The breather tube inner diameters and pressure drops are summarized in Table 7.

TABLE 7

| Example | Breather tube ID (cm) | Pressure drop (mm $H_2O$) | DOP pen (%) |
|---|---|---|---|
| 42 | 1.27 | 5.1 | 9.5 |
| 43 | 1.59 | 3.7 | 10.1 |
| 44 | 1.91 | 3.2 | 9.7 |

The data shows that for a given filter construction the larger the breather tube inner diameter the lower the pressure drop across the filter element.

Various modification and alterations of this invention will become apparent to those skilled in the art without departing from the scope and spirit of this invention.

What is claimed is:

1. A filter element comprising (A) substantially coextensive front and rear walls joined to each other along their peripheral edges and defining an interior space between them; the front and rear walls each comprising at least one layer of a filter material, and the rear wall, including said layer of filter material, having an opening that provides access to the interior space defined by the front and rear walls, (B) a porous layer contained between the front and rear walls *within the interior space* substantially coextensive with the walls, which maintains the walls [is] *in* a spaced-apart relationship over substantially their entire area, and which contributes no more than 50% of the total pressure drop across the filter element, *said porous layer comprising material selected from the group consisting of woven webs, nonwoven webs, loose fibers, fiber batts, loose particulate material, particulate material bonded together in a porous matrix, or combinations thereof,* and (C) a breather tube having one end that communicates through said opening with the *porous layer within the* interior space between the front and rear walls, and adapted at its other end for securing the filter element to a respirator face piece,

*the air being drawn through the front and rear walls into the porous layer within the space between the front and rear walls, and from the interior space through the breather tube into a respirator face piece.*

2. The filter element of claim 1 wherein said front and rear walls and said porous layer are joined together along their peripheral edges.

3. The filter element of claim 1 wherein said filter element is round.

4. The filter element of claim 1 further comprising flexible cover layers disposed over the exterior surface of the filter element.

5. The filter element of claim 4 wherein said cover layers comprise polyolefin.

6. The filter element of claim 1 wherein said at least one layer of filter material comprises material selected from the group consisting of nonwoven microfiber webs, fibrillated film webs, air-laid webs, carded webs, or combinations thereof.

7. The filter element of claim 6 wherein said at least one layer of filter material comprises material selected from the group consisting of polyolefin, polycarbonate, polyester, polyurethane, polyamide, glass, cellulose, carbon, alumina, or combinations thereof.

8. The filter element of claim 1 wherein said at least one layer of filter material comprises a plurality of layers of electrically charged, nonwoven, blown microfiber web.

9. The filter element of claim 8 wherein said electrically charged, nonwoven, blown microfiber web comprises polyolefin.

10. The filter element of claim 8 wherein said electrically charged, nonwoven, blown microfiber web comprises polypropylene.

11. The filter element of claim 1 wherein said at least one layer of filter element comprises sorbent particle-loaded fibrous web.

12. The filter element of claim 11 wherein said sorbent particle-loaded fibrous web is selected from the group consisting of alumina-particle-loaded or carbon-loaded web.

[13. The filter element of claim 1 wherein said porous layer comprises material selected from the group consisting of woven webs, nonwoven webs, loose fibers, fiber batts, loose particulate material, particulate material bonded together in a porous matrix, or combination thereof.]

14. The filter element of claim [13] *1* wherein said porous layer comprises material selected from the group consisting of polyolefin, polycarbonate, polyurethane, polyester, polyamide, glass, cellulose, carbon, alumina or combinations thereof.

15. The filter element of claim [13] *1* wherein said particulate material bonded together in a porous matrix comprises sorbent particles.

16. The filter element of claim 15 wherein said porous matrix comprises sorbent carbon particles bonded together with polyurethane resin.

17. The filter element of claim [13] wherein said porous layer comprises *a* nonwoven web.

18. The filter element of claim 17 wherein said nonwoven web is selected as from a group consisting of glass filter paper, air-laid web, carded web, fibrillated film web, sorbent particle-loaded fibrous web, or combinations thereof.

19. The filter element of claim 17 wherein said nonwoven web comprises a blend of staple and binder fibers bonded together at points of fiber intersection.

20. The filter element of claim 17 wherein the fiber diameter of said nonwoven web is no less than about 10 microns and the solidity of said nonwoven web is no greater than about 11 %.

21. The filter element of clahn 18 wherein said air-laid web comprises polyester.

22. The filter element of claim 18 wherein said carded web comprises polyester.

23. The filter element of claim 18 wherein said sorbent-particle-loaded fibrous web is selected from the group consisting of alumina-particle-loaded or carbon particle-loaded web.

24. The filter element of claim 1 wherein said porous layer is 0.2 cm to 4.0 cm thick.

25. The filter element of claim 24 wherein said porous layer is 0.3 cm to 1.3 cm thick.

26. The filter element of claim 1 wherein said of the breather tube is cylindrical in shape.

27. The filter element of claim 26 wherein the inner diameter of the breather tube is 1.0 to 4.0 cm.

28. The filter element of claim 27 wherein diameter of the breather tube is 1.5 to 3.5 cm.

29. The filter element of claim 1 wherein said [nonwoven web comprises the front and rear walls and the porous layer] *front and rear walls and said porous layer comprise nonwoven webs.*

30. A filter element comprising (A) substantially coextensive front and rear walls joined to each other along their peripheral edges and defining an interior space between them; the front and rear walls each comprising at least one layer of filter material, and the rear wall, including said layer of filter material having an opening that provides access to the interior or space defined by the front and rear walls, (B) a porous layer contained between the front and rear walls *within the interior space* which is substantially coextensive with the walls, which maintains the walls in a spaced-apart relationship substantially their entire area, and which contributes no more than 50% of the total pressure drop across the filter element, *said porous layer comprising material selected from the group consisting of woven webs, nonwoven webs, loose fibers, fiber batts, loose particulate material, material bonded together in a porous matrix, or combinations thereof,* and (C) a breather tube having one end that communicates through said opening with the *porous layer within the* interior space between the front and rear walls, and adapted at its other end for securing the filter element to a respirator face piece,

*the air being drawn through the front and rear walls into the porous layer within the interior space between the front and rear walls, and from the interior space through the breather tube into a respirator face piece,* wherein said filter element will permit no more than 1.5 mg penetration of silica dust having a geometric means particle diameter of 0.4–0.6 micrometer through said filter element over a 90 minute period at an air flowrate of 16 liters per minute, a pressure drop across said filter element before the 90 minute period of no more than 30 mm $H_2O$, and a pressure drop across the filter element after the 90 minute period of not more than 50 mm $H_2O$.

31. A filter element comprising (A) substantially coextensive front and rear walls joined to each other along their peripheral edges and defining an interior space between them; the front and rear walls each comprising at least one layer of a filter material, and the rear wall, including said layer of filter material, having an opening that provides accesss to the interior space defined by the front and rear walls, (B) a porous layer contained between the front and rear walls within the iterior space which is substantially coextensive with the walls, which maintains the walls in a spaced-apart relationship over substantially their entire area, and which contributes no more than 50% of the total pressure drop across the filter element, *said porous layer comprising material selected from the group consisting of woven webs, nonwoven webs, loose fibers, fiber batts, loose particulate material, particulate material bonded together in a porous matrix, or combinations thereof,* and (C) a breather tube having one end that communicates through said opening with the *porous layer within the* interior space between the front and rear walls, and adapted at its other end for securing the filter element to a respirator face piece

*the air being drawn through the front and rear walls into the porous layer within the interior space between the front and rear walls, and from the interior space through the breather tube into a respirator face piece,* wherein said filter element will permit (i) no more than about 3.0 percent penetration of 0.3 micrometer diameter particles of dioctyl phthalate contained in a stream at a concentration 100 micrograms/l, at a flow rate of 42.5 liters per minute, and (ii) no more than 1.5 mg penetration of silica dust having a geometric means particle diameter of 0.4–0.6 micrometer through said filter element over a 90 minute period at an air flowrate of 16 liters per minute, a pressure drop across said filter element before the 90 minute period of no more than 30 mm $H_2O$, and a pressure drop across the filter element after the 90 minute period of not more than 50 mm of $H_2O$.

32. The filter element of claim 32 wherein said penetration of 0.3 micrometer diameter particles of dioctyl phthalate is about 0.03 percent.

33. A filter element comprising (A) substantially coextensive front and rear walls joined to each other along their peripheral edges and defining an interior space between them; the front and rear walls each comprising at least one layer of a filter material, and the rear wall, including said layer of filter material, having an opening that provides access to the interior space defined by the front and rear walls, (B) a porous layer contained between the front and rear walls *within the interior space* which is substantially coextensive with the walls, which maintains the walls in a spaced-apart relationship over substantially their entire area, and which contributes no more than 50% of the total pressure drop across the filter element, *said porous layer comprising material selected from the group consisting of woven webs, nonwoven webs, loose fibers, fiber batts, loose particulate material, particulate material bonded together in a porous matrix, or combinations thereof,* and (C) a breather tube having one end that communicates through said opening with the *porous layer within the* interior space between the front and rear walls, and adapted at its other end for securing the filter element to a respirator face piece,

*the air being drawn through the front and rear walls into the porous layer within the space between the front and rear walls, and from the interior space through the breather tube into a respirator face piece,* wherein said filter element will permit no more than 1.5 mg penetration of lead fume penetration, through said filter element over a 312 minute period at an air flowrate of 16 liters per minute, a pressure drop across said filter element before the 312 minute period of no more than 30 mm of $H_2O$, and a pressure drop across the filter element after the 312 minute period of not more than 50 mm of $H_2O$.

34. One or more filter elements of claim 1 in combination with a respirator comprising a face piece.

35. One or more filter elements of claim 30 in combination with a respirator comprising a face piece.

36. One or more filter elements of claim 31 in combination with a respirator comprising a face piece.

37. One or more filter elements of claim 33 in combination with a respirator comprising a face piece.

[38. A method of filtering air comprising drawing air to be filtered through either the front or rear wall of a filter element comprising (A) substantially coextensive front and rear walls joined to each other along their peripheral edges and defining an interior space between them; the front and rear walls each comprising at least one layer of a filter material, and the rear wall, including said layer of filter material, having an opening that provides access to the interior space defined by the front and rear walls, (B) a porous layer contained between the front and rear walls which is substantially coextensive with the walls, which maintains the walls in a spaced-apart relationship over substantially their entire area, and which contributes no more than 50% of the total pressure drop across the filter element, and (C) a breather tube having one end that communicates through said opening with the interior space between the front and rear walls, and adapted at its other end for securing the filter element to a respirator face piece, the air being drawn into the interior space between the front and rear walls, and from the interior space through the breather tube into a respirator face piece.]

39. The filter element of claim 1 wherein said front and rear walls are joined to each other along their peripheral edges by ultrasonic welding.

40. The filter element of claim 1 wherein the front and rear walls comprise electrically charged, nonwoven, blown micro fiber web joined to each other along their peripheral edges by ultrasonic welding, and the porous layer comprises nonwoven web comprising a blend of staple fibers bonded together at points of fiber intersection.

41. The filter element of claim 40 further comprising flexible cover layers disposed over the exterior surface of said filter element.

* * * * *

UNITED STATES PATENT AND TRADEMARK OFFICE

CERTIFICATE OF CORRECTION

PATENT NO. : Re, 35,062
DATED : October 17, 1995
INVENTOR(S) : Gerald M. Brostrom, Daniel A. Japuntich and Sabrina M. Yard It is certified that error appears in the above-indentified patent and that said Letters Patent is hereby corrected as shown below:

Col. 1, line 36 "(1969)" should be -- (1970) --

Col. 1, line 52 "(Cove)" should be -- (Cover) --

Col. 2, line 67 "they be" should read -- they can be --

Col. 3, line 47 "comprises front" should read -- comprises a front --

Col. 3, line 49 "spsce" should read -- space --

Col. 4, line 40 "CID)" should read -- (ID) --

Col. 4, line 56 "2,4" should read -- 3,4 --

Col. 5 , line 15 "my" should read -- may --

Col. 9, line 50 "construction diameter" should read -- construction, diameter --

Col. 10, line50 "filter evenly" should read -- filter element surfaces. The inspected filter elements were evenly --

Col. 12, line 6 "*the space*" should read -- *the interior space* --

Col. 12, line 22 "webs, or" should read -- webs, sorbent-particle-loaded fibrous webs, glass filter paper, or --

Col. 12, line 43 "carbon-loaded" should read -- carbon-particle-loaded --

Col. 12, line 60 after "[13]", insert -- *1* --

Col. 12, line 63 delete "as"

UNITED STATES PATENT AND TRADEMARK OFFICE

CERTIFICATE OF CORRECTION

PATENT NO. : Re, 35,062
DATED : October 17, 1995
INVENTOR(S) : Gerald M. Brostrom, Daniel A. Japuntich and Sabrina M. Yard It is certified that error appears in the above-indentified patent and that said Letters Patent is hereby corrected as shown below:

Col. 13, line 7 "clahn" should read -- claim --

Col. 13, line 13 "carbon particle-" should read -- carbon-particle- --

Col. 13, line 19 delete "of the"

Col. 13, line 23 "wherein diameter" should read -- wherein the inner diameter --

Col. 13, line 35 delete "or"

Col. 13, line 40 "relationship substantially" should read
-- relationship over substantially --

Col. 13, line 45 "*material, material*" should read
-- *material, particulate material* --

Col. 14, line 42 "32" should read -- 31 --

Col. 16, line 21 "micro fiber" should read -- microfiber --

Signed and Sealed this
Twelfth Day of March, 1996

*Attest:*

*Attesting Officer*

Bruce Lehman

BRUCE LEHMAN

*Commissioner of Patents and Trademarks*